United States Patent
Hashimoto et al.

(10) Patent No.: US 9,909,230 B2
(45) Date of Patent: Mar. 6, 2018

(54) SEED SELECTION AND GROWTH METHODS FOR REDUCED-CRACK GROUP III NITRIDE BULK CRYSTALS

(71) Applicants: SixPoint Materials, Inc., Buellton, CA (US); SEOUL SEMICONDUCTOR CO., LTD., Ansan-si, Gyeonggi-do (KR)

(72) Inventors: Tadao Hashimoto, Santa Barbara, CA (US); Edward Letts, Buellton, CA (US); Daryl Key, La Canada, CA (US)

(73) Assignee: SixPoint Materials, Inc., Buellton, CA (US)

( * ) Notice: Subject to any disclaimer, the term of this patent is extended or adjusted under 35 U.S.C. 154(b) by 76 days.

(21) Appl. No.: 15/004,464

(22) Filed: Jan. 22, 2016

(65) Prior Publication Data

US 2016/0215410 A1 Jul. 28, 2016

Related U.S. Application Data

(60) Provisional application No. 62/106,709, filed on Jan. 22, 2015.

(51) Int. Cl.
*C30B 7/10* (2006.01)
*C30B 29/40* (2006.01)
*G01N 23/207* (2018.01)

(52) U.S. Cl.
CPC ............ *C30B 7/105* (2013.01); *C30B 29/406* (2013.01); *G01N 23/207* (2013.01); *G01N 2223/602* (2013.01)

(58) Field of Classification Search
CPC combination set(s) only.
See application file for complete search history.

(56) References Cited

U.S. PATENT DOCUMENTS

| | | | |
|---|---|---|---|
| 5,868,837 | A | 2/1999 | DiSalvo et al. |
| 6,273,948 | B1 | 8/2001 | Porowski et al. |

(Continued)

FOREIGN PATENT DOCUMENTS

| | | |
|---|---|---|
| EP | 2258890 A1 | 12/2010 |
| WO | WO2007/008198 A1 | 1/2007 |

(Continued)

OTHER PUBLICATIONS

PCT/US2016/014522 International Search Report and Written Opinion dated Apr. 4, 2016, pp. 11.

(Continued)

*Primary Examiner* — Duy Vu N Deo
*Assistant Examiner* — Erin F Bergner
(74) *Attorney, Agent, or Firm* — Strategic Innovation IP Law Offices, P.C.

(57) ABSTRACT

In one instance, the invention provides a method of growing bulk crystal of group III nitride using a seed crystal selected by (a) measuring x-ray rocking curves of a seed crystal at more than one point, (b) quantifying the peak widths of the measured x-ray rocking curves, and (c) evaluating the distribution of the quantified peak widths. The invention also includes the method of selecting a seed crystal for growing bulk crystal of group III nitride.

The bulk crystal of group III nitride can be grown in supercritical ammonia or a melt of group III metal using at least one seed selected by the method above.

25 Claims, 2 Drawing Sheets

(56) References Cited

U.S. PATENT DOCUMENTS

| | | |
|---|---|---|
| 6,656,615 B2 | 12/2003 | Dwiliński et al. |
| 7,078,731 B2 | 7/2006 | D'Evelyn et al. |
| 7,132,730 B2 | 11/2006 | Dwiliński et al. |
| 7,160,388 B2 | 1/2007 | Dwiliński et al. |
| 2007/0234946 A1* | 10/2007 | Hashimoto ............... C30B 7/10 117/71 |
| 2007/0257334 A1* | 11/2007 | Leibiger ................. C30B 25/00 257/615 |
| 2009/0309105 A1 | 12/2009 | Letts et al. |
| 2013/0065036 A1 | 3/2013 | Hayashi et al. |
| 2013/0323490 A1 | 12/2013 | D'Evelyn et al. |

FOREIGN PATENT DOCUMENTS

| | | |
|---|---|---|
| WO | WO2007/117689 A2 | 10/2007 |
| WO | WO2016/118862 A1 | 7/2016 |

OTHER PUBLICATIONS

Wang, et al., Journal of Crystal Growth, vol. 318 (2011), pp. 1030-1033.

\* cited by examiner

SEED SELECTION AND GROWTH METHODS FOR REDUCED-CRACK GROUP III NITRIDE BULK CRYSTALS

CROSS REFERENCE TO RELATED APPLICATIONS

This application claims benefit of priority to U.S. application Ser. No. 62/106,709 filed Jan. 22, 2015, entitled "Seed Selection and Growth Methods for Reduced-Crack Group III Nitride Bulk Crystals," inventors Tadao Hashimoto, Edward Letts, and Daryl Key, and this application is also related to the following:

PCT Utility Patent Application Serial No. US2005/024239, filed on Jul. 8, 2005, by Kenji Fujito, Tadao Hashimoto and Shuji Nakamura, entitled "METHOD FOR GROWING GROUP III-NITRIDE CRYSTALS IN SUPERCRITICAL AMMONIA USING AN AUTOCLAVE,";

U.S. Utility patent application Ser. No. 11/784,339, filed on Apr. 6, 2007, by Tadao Hashimoto, Makoto Saito, and Shuji Nakamura, entitled "METHOD FOR GROWING LARGE SURFACE AREA GALLIUM NITRIDE CRYSTALS IN SUPERCRITICAL AMMONIA AND LARGE SURFACE AREA GALLIUM NITRIDE CRYSTALS," which application claims the benefit under 35 U.S.C. Section 119(e) of U.S. Provisional Patent Application Ser. No. 60/790,310, filed on Apr. 7, 2006, by Tadao Hashimoto, Makoto Saito, and Shuji Nakamura, entitled "A METHOD FOR GROWING LARGE SURFACE AREA GALLIUM NITRIDE CRYSTALS IN SUPERCRITICAL AMMONIA AND LARGE SURFACE AREA GALLIUM NITRIDE CRYSTALS,";

U.S. Utility Patent Application Ser. No. 60/973,602, filed on Sep. 19, 2007, by Tadao Hashimoto and Shuji Nakamura, entitled "GALLIUM NITRIDE BULK CRYSTALS AND THEIR GROWTH METHOD,";

U.S. Utility patent application Ser. No. 11/977,661, filed on Oct. 25, 2007, by Tadao Hashimoto, entitled "METHOD FOR GROWING GROUP III-NITRIDE CRYSTALS IN A MIXTURE OF SUPERCRITICAL AMMONIA AND NITROGEN, AND GROUP III-NITRIDE CRYSTALS GROWN THEREBY," now U.S. Pat. No. 7,803,344;

U.S. Utility Patent Application Ser. No. 61/067,117, filed on Feb. 25, 2008, by Tadao Hashimoto, Edward Letts, Masanori Ikari, entitled "METHOD FOR PRODUCING GROUP III-NITRIDE WAFERS AND GROUP III-NITRIDE WAFERS," now U.S. Pat. No. 8,728,234;

U.S. Utility Patent Application Ser. No. 61/058,900, filed on Jun. 4, 2008, by Edward Letts, Tadao Hashimoto, Masanori Ikari, entitled "METHODS FOR PRODUCING IMPROVED CRYSTALLINITY GROUP III-NITRIDE CRYSTALS FROM INITIAL GROUP III-NITRIDE SEED BY AMMONOTHERMAL GROWTH," now U.S. Pat. No. 8,728,234;

U.S. Utility Patent Application Ser. No. 61/058,910, filed on Jun. 4, 2008, by Tadao Hashimoto, Edward Letts, Masanori Ikari, entitled "HIGH-PRESSURE VESSEL FOR GROWING GROUP III NITRIDE CRYSTALS AND METHOD OF GROWING GROUP III NITRIDE CRYSTALS USING HIGH-PRESSURE VESSEL AND GROUP III NITRIDE CRYSTAL," now U.S. Pat. Nos. 8,236,267 and 8,420,041;

U.S. Utility Patent Application Ser. No. 61/131,917, filed on Jun. 12, 2008, by Tadao Hashimoto, Masanori Ikari, Edward Letts, entitled "METHOD FOR TESTING III-NITRIDE WAFERS AND III-NITRIDE WAFERS WITH TEST DATA," now U.S. Pat. Nos. 8,357,243, 8,577,043, and 8,585,822;

U.S. Utility Patent Application Ser. No. 61/106,110, filed on Oct. 16, 2008, by Tadao Hashimoto, Masanori Ikari, Edward Letts, entitled "REACTOR DESIGN FOR GROWING GROUP III NITRIDE CRYSTALS AND METHOD OF GROWING GROUP III NITRIDE CRYSTALS,";

U.S. Utility Patent Application Ser. No. 61/694,119, filed on Aug. 28, 2012, by Tadao Hashimoto, Edward Letts, Sierra Hoff, entitled "GROUP III NITRIDE WAFER AND PRODUCTION METHOD," now U.S. Pat. No. 8,921,231;

U.S. Utility Patent Application Ser. No. 61/705,540, filed on Sep. 25, 2012, by Tadao Hashimoto, Edward Letts, Sierra Hoff, entitled "METHOD OF GROWING GROUP III NITRIDE CRYSTALS," not U.S. Pat. No. 9,202,872;

all of which are incorporated by reference herein in their entirety as if put forth in full below.

BACKGROUND

Field of the Invention

The invention relates to a bulk crystal of semiconductor material used to produce semiconductor wafers for various devices including optoelectronic devices such as light emitting diodes (LEDs) and laser diodes (LDs), and electronic devices such as transistors. More specifically, the invention provides a bulk crystal of group III nitride such as gallium nitride. The invention also provides a method of selecting seed crystals for growth of group III nitride bulk crystals.

Description of the Existing Technology

This document refers to several publications and patents as indicated with numbers within brackets, e.g., [x]. Following is a list of these publications and patents:

[1] R. Dwiliński, R. Doradziński, J. Garczyński, L. Sierzputowski, Y. Kanbara, U.S. Pat. No. 6,656,615.
[2] R. Dwiliński, R. Doradziński, J. Garczyński, L. Sierzputowski, Y. Kanbara, U.S. Pat. No. 7,132,730.
[3] R. Dwiliński, R. Doradziński, J. Garczyński, L. Sierzputowski, Y. Kanbara, U.S. Pat. No. 7,160,388.
[4] K. Fujito, T. Hashimoto, S. Nakamura, International Patent Application No. PCT/US2005/024239, WO07008198.
[5] T. Hashimoto, M. Saito, S. Nakamura, International Patent Application No. PCT/US2007/008743, WO07117689. See also US20070234946, U.S. application Ser. No. 11/784,339 filed Apr. 6, 2007.
[6] D' Evelyn, U.S. Pat. No. 7,078,731.
[7] Wang et al., Journal of Crystal Growth volume 318 (2011) p 1030.

Each of the references listed in this document is incorporated by reference in its entirety as if put forth in full herein, and particularly with respect to their description of methods of making and using group III nitride substrates.

Gallium nitride (GaN) and its related group III nitride alloys are the key material for various optoelectronic and electronic devices such as LEDs, LDs, microwave power transistors, and solar-blind photo detectors. Currently LEDs are widely used in displays, indicators, general illuminations, and LDs are used in data storage disk drives. However, the majority of these devices are grown epitaxially on heterogeneous substrates, such as sapphire and silicon carbide because GaN substrates are extremely expensive compared to these heteroepitaxial substrates. The heteroepitaxial growth of group III nitride causes highly defected or even cracked films, which hinder the realization of high-end optical and electronic devices, such as high-brightness LEDs for general lighting or high-power microwave transistors.

To solve fundamental problems caused by heteroepitaxy, it is indispensable to utilize crystalline group III nitride wafers sliced from bulk group III nitride crystal ingots. For the majority of devices, crystalline GaN wafers are favorable because it is relatively easy to control the conductivity of the wafer and GaN wafer will provide the smallest lattice/ thermal mismatch with device layers. However, due to the high melting point and high nitrogen vapor pressure at elevated temperature, it has been difficult to grow GaN crystal ingots. Currently, the majority of commercially available GaN substrates are produced by a method called hydride vapor phase epitaxy (HVPE). HVPE is one of vapor phase methods, which has difficulty in reducing dislocation density less than $10^5$ cm$^{-2}$.

To obtain high-quality GaN substrates for which dislocation density is less than $10^5$ cm$^{-2}$, various growth methods such as ammonothermal growth, flux growth, high-temperature solution growth have been developed. Ammonothermal method grows group III nitride crystals in supercritical ammonia [1-6]. The flux method and the high-temperature solution growth use a melt of group III metal.

Recently, high-quality GaN substrates having dislocation density less than $10^5$ cm$^{-2}$ can be obtained by ammonothermal growth. Since the ammonothermal method can produce a true bulk crystal, one can grow one or more thick crystals and slice them to produce GaN wafers. We have been developing bulk crystals of GaN by the ammonothermal method. However, we found it quite challenging to avoid cracking of bulk crystals, especially when the total thickness of the bulk crystal exceeds 1 mm. We believe that the cracking problem in bulk group III nitride is a universal problem for any bulk growth methods including the ammonothermal method. Thus, this invention is intended to obtain crack-free bulk group III nitride crystals using any bulk growth method, such as growth in supercritical ammonia or from a melt of group III metals.

SUMMARY OF THE INVENTION

In one instance, the invention provides a method of growing bulk crystal of group III nitride using a seed crystal selected by (a) measuring x-ray rocking curves of the seed crystal at more than one point, (b) quantifying the peak widths of the measured x-ray rocking curves, and (c) evaluating the distribution of the quantified peak widths. The invention also includes the method of selecting a seed crystal for growing bulk crystal of group III nitride.

BRIEF DESCRIPTION OF THE DRAWINGS

Referring now to the drawings in which like reference numbers represent corresponding parts throughout.

DETAILED DESCRIPTION OF THE INVENTION

Overview

Figure 1:
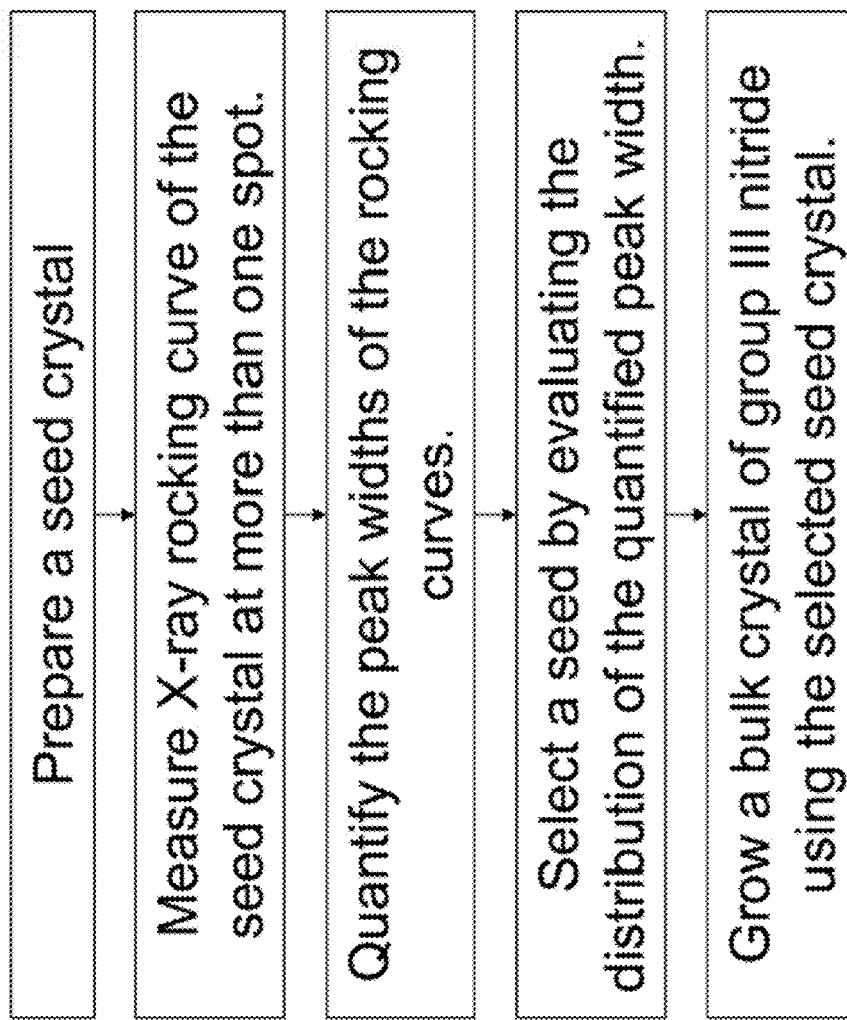
FIG. 1 is an example of a process flow of this invention.

The bulk crystal of the present invention is typically sliced to produce group III nitride wafers suitable for fabricating various optoelectronic and electronic devices such as LEDs, LD, transistors, and photodetectors by known techniques. Many optoelectronic and electronic devices are fabricated with thin films of group III nitride alloys (i.e. alloys of GaN, AN and InN). The group III nitride alloys are typically expressed as $Ga_xAl_yIn_{1-x-y}N$ ($0 \le x \le 1$, $0 \le x+y \le 1$). Since the group III metallic elements (i.e. Al, Ga, In) shows similar chemical characteristics, nitrides of these group III elements makes alloys or solid solution. In addition, crystal growth nature of these group III nitrides are quite similar.

Due to limited availability and high cost of single crystalline substrates of group III nitride, these devices have been fabricated on so-called heteroepitaxial substrates such as sapphire and silicon carbide. Since the heteroepitaxial substrates are chemically and physically different from the group III nitride, the device typically has a high density of dislocations ($10^8$~$10^{10}$ cm$^{-2}$) generated at the interface between the heteroepitaxial substrate and the device layer. Such dislocations deteriorate performance and reliability of devices, thus substrates composed of crystalline group III nitride such as GaN and AlN are favorable.

Currently, the majority of commercially available GaN substrates is produced with HVPE, in which it is difficult to reduce the dislocation density to less than $10^5$ cm$^{-2}$. Although the dislocation density of HVPE-GaN substrates is a few orders of magnitude lower than GaN film on heteroepitaxial substrates, the dislocation density is still a few orders of magnitude higher than typical silicon devices in electronics. To achieve higher device performance, lower dislocation density is required.

To attain dislocation density less than $10^5$ cm$^{-2}$, ammonothermal growth, which utilizes supercritical ammonia, has been developed. The ammonothermal method can produce GaN substrates with dislocation density less than $10^5$ cm$^{-2}$. One advantage of the ammonothermal method is that bulk crystals having a thickness larger than 1 mm can be grown. The ammonothermal method can also be used to grow crystals having various dopants such as donors (i.e. electron), acceptors (i.e. hole) or magnetic dopants. However, it is challenging to obtain a bulk crystal over 1 mm thick without cracking. It is a common practice to evaluate seed crystals and select a good seed for the ammonothermal growth. For example, Wang et al., disclosed a procedure to evaluate FWHM of X-ray rocking curve to select a good seed [7]. Nevertheless, we have experienced cracking problem even with such selection procedure. Although the origin and mechanism for crack formation are not well known, a possible cause would be stress accumulation inside the crystal due to a slight mismatch of thermal expansion coefficient or other physical properties between the seed crystal and grown crystal. To produce group III nitride substrates without cracks, it is necessary to obtain crack-free bulk crystal of group III nitride.

Technical Description of the Invention

In an effort to reduce or eliminate cracking inside the bulk crystal of group III nitride having thickness larger than 1 mm, the current invention provides a method of making a bulk crystal of group III nitride in which a seed crystal is selected by (a) measuring x-ray rocking curves of the seed crystal at more than one point, (b) quantifying the peak widths of the measured x-ray rocking curves, and (c) evaluating the distribution of the quantified peak widths. FIG. 1 presents a process flow of this invention.

First, a seed crystal for growing bulk crystal of group III nitride such as GaN is prepared. Seed crystal is preferably a single crystal of group III nitride such as GaN. The orientation of the seed crystal can be c-plane, a-plane, m-plane or other semipolar planes, although c-plane crystal is preferable. The single-crystal seed may be grown by hydride vapor-phase epitaxy (HVPE), molecular beam epitaxy (MBE), metal organic vapor-phase epitaxy (MOVPE), ammonothermal growth, flux method, high-pressure solution growth or other method.

Then, the seed crystal is measured with X-ray diffractometer to obtain rocking curves from more than one spot of the seed crystal. One example of selecting the measurement location is a straight line along one crystallographic orientation such as m-direction or a-direction. Another example is to select points at intersections or within a square grid plotted over the seed's face. Another example is to take a statistically significant number of random measurements of the seed crystal's structure over the seed's face.

When a c-plane group III nitride crystal such as c-plane GaN is used, off-axis diffraction such as 201 and 102 reflections is preferably used. This is because the off-axis reflections turned out to be more sensitive to the quality of the seed crystals for growing bulk crystals. Consequently, it is helpful to first determine which directions are more sensitive to crystal structure of the seed crystal for the particular seed used (e.g. c-plane, m-plane, a-plane), and then use those directions in measuring quality of crystal structure at various points across the surface of the seed.

To quantify the peak width of the X-ray rocking curve, FWHM is commonly used although other methods of quantifying the peak width is also used. As commonly known, the peak width of the X-ray rocking curve represents the quality of microstructure of the crystal. The peak width is typically measured in the unit of arcsec, arcmin, or degree.

To evaluate the distribution of the peak widths, statistic value such as a standard deviation can be used. Alternately, one can plot the peak width data on a graph, and visually determine the distribution of the data. The magnitude of data scattering can be evaluated in an absolute value with a unit of arcsec, arcmin or degree. Alternately, the magnitude of data scattering can be evaluated relative to a representative value such as a mean value of all data.

If a standard deviation and a mean value is used to select a good seed crystal, the standard deviation is preferably less than 30% of the mean value, more preferably less than 20% of the mean value, or more preferably less than 10% of the mean value.

The selected seed crystal will be used to grow a bulk crystal of group III nitride such as bulk GaN. Depending on the growth method of a bulk crystal, one can select most preferable seed orientation and polarity. For example, when a bulk crystal is grown in supercritical ammonia, nitrogen polar c-plane GaN is preferably used.

Example 1

Figure 2:
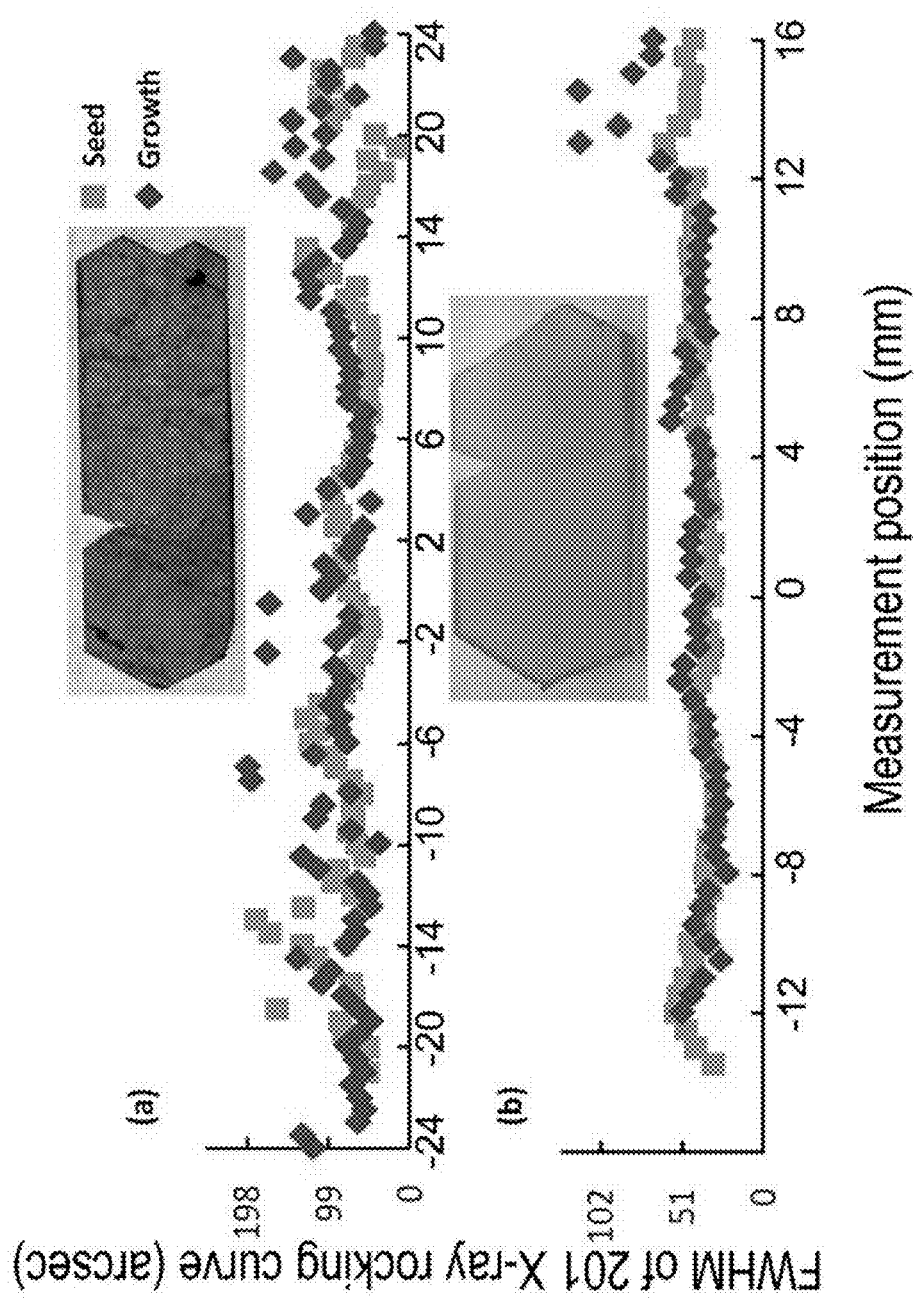
FIG. 2 shows full width half maximum (FWHM) of 201 X-ray rocking curves from seed crystals (square dots), FWHM of 201 X-ray rocking curves from bulk GaN crystals using the corresponding seeds (diamond dots), and a photograph of a wafer sliced from the corresponding bulk GaN crystals. (a) for a seed with scattered distribution of FWHM, (b) for a seed with less scattered distribution of FWHM. The zero-point is at approximately the center of the seed's face along the longest line on an m-plane. XRD data in the examples was collected at various points across the seed crystal's face and along this line.

Single crystalline GaN seed crystal having a basal plane of c-plane was prepared with HVPE. The thickness of the GaN seed was approximately 430 microns. X-ray rocking curves from 201 reflection were recorded from multiple spots of the nitrogen polar side of the seed crystal. The measurement was conducted along the m-direction with the spot separation of 0.5 mm. The peak width is quantified with FWHM in arcsec. The square dots in FIG. 2 (a) show FWHM at each measurement spot. As shown in the FIG. 2(a) the FWHM values have a large scattering. The mean value of the FWHM was 78 arcsec and the standard deviation was 29 arcsec, which was 37% of the mean value. The data scattering is seen throughout the scanned line.

Then, a bulk crystal of GaN was grown in supercritical ammonia using a high-pressure reactor. The chamber within the high-pressure reactor was divided into a lower part and an upper part with baffle plates. Approximately 15 g of polycrystalline GaN is used as a nutrient and approximately 3.1 g of sodium is used as a mineralizer. Mineralizer and the seed crystal were placed in the lower part of the high-pressure reactor and the nutrient was placed in the upper part of the high-pressure reactor. Then, the high-pressure reactor was sealed, pumped to a vacuum and filled with anhydrous liquid ammonia. The volumetric ammonia fill factor was approximately 53%. The high-pressure reactor was heated at about 510~520° C. to allow crystal growth of GaN on the seed. After sufficient amount of time, the ammonia was released and the high-pressure reactor was cooled. The resultant bulk GaN crystal has a thickness of approximately 5 mm.

X-ray rocking curves from 201 reflection were measured at multiple spots on the surface of the grown bulk GaN crystal as described above and as described in Example 2. The FWHMs are plotted in FIG. 2(a) with diamond dots. As shown in the figure, the FWHMs from the grown bulk crystal also showed large scattering. The mean value of the FWHM was 89 arcsec and the standard deviation was 38 arcsec, which was 43% of the mean value. Then, the bulk crystal was sliced into wafers with a multiple wire saw. The inset picture in FIG. 2(a) is a photograph of the sliced wafer. The wafer had numerous cracks.

Example 2

Similar to Example 1, a c-plane GaN seed crystal was prepared with HVPE. The thickness of the GaN seed was approximately 430 microns. X-ray rocking curves from 201 reflection were recorded from multiple spots of the nitrogen polar side of the seed crystal. The measurement was conducted along a m-direction with spot separation of 0.5 mm. The peak width is quantified with FWHM in arcsec. The square dots in FIG. 2 (b) show FWHM at each measurement spot. As shown in the FIG. 2(b) the FWHM values have a small scattering. The mean value of the FWHM was 41 arcsec and the standard deviation was 7 arcsec, which was 17% of the mean value.

Then bulk GaN was grown on this seed crystal in a similar way as in Example 1. The FWHMs of 201 X-ray rocking curves from multiple spots on the grown bulk crystal are plotted with diamond dots in FIG. 2(b), showing small data scattering. The mean value of the FWHM was 48 arcsec and the standard deviation was 18 arcsec, which was 38% of the mean value. As seen in FIG. 2(b) between the +12 and +16 mm positions, the large standard deviation is caused by an edge effect of the measurement, causing XRD data to be less reliable. The center portion of the wafer has much less data scattering. A wafer sliced from this bulk GaN crystal showed much reduced cracks as shown in the picture of FIG. 2(b). The crack density was less than 1 $cm^{-2}$. Comparing Example 1 and Example 2, we discovered a strong correlation between the data scattering of peak widths of X-ray rocking curve from the seed crystal and crack density in the bulk crystal using the seed.

The evaluation of the data scattering can be performed by combining a standard deviation, visual judgment and other criteria. For example, if we use the center portion of the data from the seed crystal in this example (FIG. 2(b)), the standard deviation can be smaller than 10% of the mean value. This way one can eliminate the edge effect of the measurement. Taking a correlation between the data scattering of the rocking curve peak width and cracking density, one can obtain a crack-free bulk crystal.

Advantages and Improvements

The bulk GaN crystal obtained with the method disclosed in this invention contains no or reduced amount of cracks. The obtained crack-free bulk GaN crystals are sliced into wafers. These wafers are used for optical devices such as LEDs and laser diodes or electronic devices such as high-power transistors. Since cracks deteriorate performances and reliability of these devices significantly, this invention can improve the device performance and reliability.

Therefore, the following are disclosed by way of example and not by way of limitation on the scope of the invention:

1. A method of growing a bulk crystal of group III nitride having a composition of $Ga_{x1}Al_{y1}In_{1-x1-y1}N$ ($0 \le x1 \le 1$, $0 \le x1+y1 \le 1$) comprising:
   (a) measuring x-ray rocking curves of the seed crystal at more than one point;
   (b) quantifying peak widths of the measured x-ray rocking curves;
   (c) comparing a measure of the distribution of the quantified peak widths to an acceptable value; and
   (d) growing single crystal $Ga_{x1}Al_{y1}In_{1-x1-y1}N$ on a face of the seed crystal having the acceptable value of the distribution of quantified peak widths to form the bulk crystal of group III nitride.
2. A method according to paragraph 1 wherein the method of quantifying the peak widths comprises calculating a full width half maximum of peaks of the x-ray rocking curves.
3. A method according to paragraph 1 or paragraph 2 wherein the distribution of the quantified peak widths is determined with a standard deviation.
4. A method according to paragraph 3 wherein the standard deviation is less than 30% of the mean value of the quantified peak widths.
5. A method according to paragraph 3 wherein the standard deviation is less than 20% of the mean value of the quantified peak widths.
6. A method according to paragraph 3 wherein the standard deviation is less than 10% of the mean value of the quantified peak widths.
7. A method according to any one of paragraph 1 through paragraph 6 wherein the seed crystal is primarily c-plane oriented and the x-ray rocking curves are measured on one or more off-axis planes.
8. A method according to paragraph 7, wherein the x-ray rocking curves are measured in the m-direction.
9. A method according to paragraph 7, wherein the off-axis plane is 201 reflection.
10. A method according to paragraph 7, wherein the off-axis plane is 102 reflection.
11. A method according to any one of paragraph 1 through paragraph 10 wherein the seed crystal is gallium nitride.
12. A method according to any one of paragraph 1 through paragraph 11 wherein the group III nitride is GaN.
13. A method according to any one of paragraph 1 through paragraph 12 wherein the group III nitride is grown in supercritical ammonia.
14. A method according to any one of paragraph 1 through paragraph 13 wherein the bulk crystal of group III nitride has crack density less than 1 $cm^{-2}$.
15. A method of selecting a seed crystal for growing bulk crystal of group III nitride having a composition of $Ga_{x1}Al_{y1}In_{1-x1-y1}N$ ($0 \le x1 \le 1$, $0 \le x1+y1 \le 1$) comprising,
   (a) measuring x-ray rocking curves of a seed crystal at more than one point;
   (b) quantifying peak widths of the measured x-ray rocking curves;
   (c) comparing a measure of the distribution of the quantified peak widths to an acceptable value; and
   (d) designating the seed crystal as acceptable or unacceptable based on said measure of the distribution of quantified peak widths.
16. A method according to paragraph 15 wherein the method of quantifying the peak widths comprises calculating a full width half maximum of peaks of the x-ray rocking curves.
17. A method according to paragraph 15 or paragraph 16 wherein the distribution of the quantified peak widths is determined with a standard deviation.
18. A method according to paragraph 17 wherein the standard deviation is less than 30% of the mean value of the quantified peak widths.
19. A method according to paragraph 17 wherein the standard deviation is less than 20% of the mean value of the quantified peak widths.
20. A method according to paragraph 17 wherein the standard deviation is less than 10% of the mean value of the quantified peak widths.
21. A method according to any one of paragraph 15 through paragraph 20 wherein the seed crystal is primarily c-plane oriented and the x-ray rocking curves are measured on one or more off-axis planes.
22. A method according to paragraph 21, wherein the x-ray rocking curves are measured in the m-direction.
23. A method according to paragraph 21, wherein the off-axis plane is 201 reflection.
24. A method according to paragraph 21, wherein the off-axis plane is 102 reflection.
25. A method according to any one of paragraph 15 through paragraph 24 wherein the seed crystal is gallium nitride.
26. A method according to any one of paragraph 15 through paragraph 25 wherein the group III nitride is GaN.
27. Bulk group III nitride grown by a method of any paragraph above.
28. A wafer of group III nitride formed by a method of any paragraph above.

Possible Modifications

Although the preferred embodiment describes bulk crystals of GaN, similar benefit of this invention can be expected for other group III nitride alloys of various compositions, such as AlN, AlGaN, InN, InGaN, or GaAlInN.

Although the preferred embodiment describes GaN seed crystal having thickness about 430 microns, similar benefit of this invention can be expected for other thicknesses between 100 microns to 2000 microns.

Although the preferred embodiment describes ammonothermal growth, similar benefit of this invention can be expected for other bulk growth methods such as a flux method or high-pressure, high-temperature solution growth. In the flux method, a group III metal and a flux such as sodium are melted together, and nitrogen then dissolves into the melt. One flux method is disclosed in U.S. Pat. No.

5,868,837. One suitable high-pressure, high-temperature solution growth method is disclosed in U.S. Pat. No. 6,273,948 B1. Each of these patents is incorporated by reference herein.

Although the preferred embodiment describes a seed crystal of approximately 50 mm in size, similar benefit of this invention is expected for smaller or larger seed such as 1", 2", 4", 6".

A bulk crystal as described, as made, or as used in any of the description above may have a thickness greater than or equal to: 1 mm, 2 mm, 3 mm, 4 mm, 5 mm, 6 mm, 7 mm, 8 mm, 9 mm, 10 mm, for instance.

What is claimed is:

1. A method of growing a bulk crystal of group III nitride having a composition of $Ga_{x1}Al_{y1}In_{1-x1-y1}N$ ($0 \leq x1 \leq 1$, $0 \leq x1+y1 \leq 1$) comprising:
   (a) measuring x-ray rocking curves of the seed crystal at more than one point;
   (b) quantifying peak widths of the measured x-ray rocking curves;
   (c) comparing a measure of the distribution of the quantified peak widths to an acceptable value; and
   (d) growing single crystal $Ga_{x1}Al_{y1}In_{1-x1-y1}N$ on a face of the seed crystal having the acceptable value of the distribution of quantified peak widths to form the bulk crystal of group III nitride, wherein the bulk crystal of group III nitride has a crack density less than 1 $cm^{-2}$.

2. A method according to claim 1 wherein the method of quantifying the peak widths comprises calculating a full width half maximum of peaks of the x-ray rocking curves.

3. A method according to claim 1 wherein the distribution of the quantified peak widths is determined with a standard deviation.

4. A method according to claim 3 wherein the standard deviation is less than 30% of the mean value of the quantified peak widths.

5. A method according to claim 3 wherein the standard deviation is less than 20% of the mean value of the quantified peak widths.

6. A method according to claim 1 wherein the seed crystal is primarily c-plane oriented and the x-ray rocking curves are measured on one or more off-axis planes.

7. A method according to claim 6, wherein the x-ray rocking curves are measured in m-direction.

8. A method according to claim 6, wherein the off-axis plane is 201 reflection.

9. A method according to claim 6, wherein the off-axis plane is 102 reflection.

10. A method according to claim 1 wherein the seed crystal is gallium nitride.

11. A method according to claim 10 wherein the group III nitride is GaN.

12. A method according to claim 1 wherein the group III nitride is grown in supercritical ammonia.

13. A method of selecting a seed crystal for growing bulk crystal of group III nitride having a composition of $Ga_{x1}Al_{y1}In_{1-x1-y1}N$ ($0 \leq x1 \leq 1$, $0 \leq x1+y1 \leq 1$) comprising,
   (a) measuring x-ray rocking curves of a seed crystal at more than one point;
   (b) quantifying peak widths of the measured x-ray rocking curves;
   (c) comparing a measure of the distribution of the quantified peak widths to an acceptable value; and
   (d) designating the seed crystal as acceptable or unacceptable for growth of a bulk crystal of group III nitride having a crack density less than 1 $cm^{-2}$ based on said measure of the distribution of quantified peak widths.

14. A method according to claim 13 wherein the method of quantifying the peak widths comprises calculating a full width half maximum of peaks of the x-ray rocking curves.

15. A method according to claim 13 wherein the distribution of the quantified peak widths is determined with a standard deviation.

16. A method according to claim 15 wherein the standard deviation is less than 30% of the mean value of the quantified peak widths.

17. A method according to claim 15 wherein the standard deviation is less than 20% of the mean value of the quantified peak widths.

18. A method according to claim 13 wherein the seed crystal is primarily c-plane oriented and the x-ray rocking curves are measured on one or more off-axis planes.

19. A method according to claim 18, wherein the x-ray rocking curves are measured in the m-direction.

20. A method according to claim 18, wherein the off-axis plane is 201 reflection.

21. A method according to claim 18, wherein the off-axis plane is 102 reflection.

22. A method according to claim 13 wherein the seed crystal is gallium nitride.

23. A method according to claim 22 wherein the group III nitride is GaN.

24. A method according to claim 1, wherein the bulk crystal has a thickness larger than 1 mm.

25. A method according to claim 12, wherein the bulk crystal has a thickness larger than 1 mm.

* * * * *

UNITED STATES PATENT AND TRADEMARK OFFICE
CERTIFICATE OF CORRECTION

| | | |
|---|---|---|
| PATENT NO. | : 9,909,230 B2 | |
| APPLICATION NO. | : 15/004464 | |
| DATED | : March 6, 2018 | |
| INVENTOR(S) | : Hashimoto et al. | |

It is certified that error appears in the above-identified patent and that said Letters Patent is hereby corrected as shown below:

In the Specification

Column 1 Line 7 insert the following:
--Government Interest Statement
The invention was made with government support under award DE-AR0000445 awarded by the Department of Energy. The government has certain rights to the invention.--

Signed and Sealed this
Twenty-first Day of June, 2022

Katherine Kelly Vidal
*Director of the United States Patent and Trademark Office*